US008261423B2

(12) United States Patent
Jow et al.

(10) Patent No.: US 8,261,423 B2
(45) Date of Patent: Sep. 11, 2012

(54) METHODS FOR CRIMPING A POLYMERIC STENT ONTO A DELIVERY BALLOON

(75) Inventors: Kevin F. Jow, San Mateo, CA (US);
Arlene Sucy Yang, Belmont, CA (US);
Yunbing Wang, Sunnyvale, CA (US);
Kathleen W. Yan, Cupertino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 162 days.

(21) Appl. No.: 12/772,116

(22) Filed: Apr. 30, 2010

(65) Prior Publication Data

US 2011/0270383 A1 Nov. 3, 2011

(51) Int. Cl.
B23P 11/02 (2006.01)
B21D 39/04 (2006.01)
A61F 2/06 (2006.01)

(52) U.S. Cl. ............... 29/447; 29/508; 29/515; 29/516; 623/1.19; 623/1.49

(58) Field of Classification Search .............. 29/447, 29/557, 508, 515, 516; 623/1.19, 1.49
See application file for complete search history.

(56) References Cited

U.S. PATENT DOCUMENTS

| 5,836,965 A | 11/1998 | Jendersee et al. |
| 5,913,871 A | 6/1999 | Werneth et al. |
| 5,976,181 A | 11/1999 | Whelan et al. |
| 6,745,445 B2 | 6/2004 | Spilka |
| 6,863,683 B2 | 3/2005 | Schwager et al. |
| 7,761,968 B2 | 7/2010 | Huang et al. |
| 2002/0143382 A1 | 10/2002 | Hijlkema et al. |
| 2004/0078953 A1 | 4/2004 | Spilka |
| 2004/0106973 A1 | 6/2004 | Johnson |
| 2005/0119720 A1 | 6/2005 | Gale et al. |
| 2006/0047336 A1 | 3/2006 | Gale et al. |
| 2007/0006441 A1 | 1/2007 | McNiven et al. |
| 2007/0271763 A1 | 11/2007 | Huang et al. |
| 2007/0282433 A1 | 12/2007 | Limon et al. |
| 2007/0289117 A1 | 12/2007 | Huang et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0147164 A1 | 6/2008 | Gale et al. |
| 2008/0275537 A1 | 11/2008 | Limon |
| 2009/0001633 A1 | 1/2009 | Limon et al. |
| 2009/0088829 A1 | 4/2009 | Wang et al. |
| 2010/0004735 A1 | 1/2010 | Yang et al. |

(Continued)

FOREIGN PATENT DOCUMENTS

EP 1 295 570 3/2003

(Continued)

OTHER PUBLICATIONS

International Search Report and the Written Opinion for PCT/US2011/032283 mailed Aug. 18, 2011, 17 pgs.

(Continued)

Primary Examiner — Jermie Cozart
(74) Attorney, Agent, or Firm — Squire Sanders (US) LLP

(57) ABSTRACT

A medical device-includes a polymer stent crimped to a catheter having an expansion balloon. The stent is crimped to the balloon by a process that includes heating the stent to a temperature below the polymer's glass transition temperature to improve stent retention without adversely affecting the mechanical characteristics of the stent when later deployed to support a body lumen.

11 Claims, 2 Drawing Sheets

U.S. PATENT DOCUMENTS

2010/0025894 A1   2/2010   Kleiner et al.

FOREIGN PATENT DOCUMENTS

| WO | WO 99/55406 | 11/1999 |
| WO | WO 2007/146354 | 12/2007 |
| WO | WO 2010/151497 | 12/2010 |

OTHER PUBLICATIONS

U.S. Appl. No. 11/326,797, filed Jan. 6, 2006, Abbate et al.
U.S. Appl. No. 11/330,927, filed Jan. 11, 2006, Wu et al.

METHODS FOR CRIMPING A POLYMERIC STENT ONTO A DELIVERY BALLOON

BACKGROUND OF THE INVENTION

1. Field of the Invention

The present invention relates to drug-eluting medical devices; more particularly, this invention relates to processes for crimping a polymeric stent to a delivery balloon.

2. Background of the Invention

The art recognizes a variety of factors that affect a polymeric stent's ability to retain its structural integrity when subjected to external loadings, such as crimping and balloon expansion forces. These interactions are complex and the mechanisms of action not fully understood. According to the art, characteristics differentiating a polymeric, bio-absorbable stent scaffolding of the type expanded to a deployed state by plastic deformation from a similarly functioning metal stent are many and significant. Indeed, several of the accepted analytic or empirical methods/models used to predict the behavior of metallic stents tend to be unreliable, if not inappropriate, as methods/models for reliably and consistently predicting the highly non-linear behavior of a polymeric load-bearing, or scaffolding portion of a balloon-expandable stent. The models are not generally capable of providing an acceptable degree of certainty required for purposes of implanting the stent within a body, or predicting/anticipating the empirical data.

Moreover, it is recognized that the state of the art in medical device-related balloon fabrication, e.g., non-compliant balloons for stent deployment and/or angioplasty, provide only limited information about how a polymeric material might behave when used to support a lumen within a living being via plastic deformation of a network of rings interconnected by struts. In short, methods devised to improve mechanical features of an inflated, thin-walled balloon structure, most analogous to mechanical properties of a pre-loaded membrane when the balloon is inflated and supporting a lumen, simply provides little, if any insight into the behavior of a deployed polymeric stent scaffolding. One difference, for example, is the propensity for fracture or cracks to develop in a stent scaffolding. The art recognizes the mechanical problem as too different to provide helpful insights, therefore, despite a shared similarity in class of material. At best, the balloon fabrication art provides only general guidance for one seeking to improve characteristics of a balloon-expanded, bio-absorbable polymeric stent.

Polymer material considered for use as a polymeric stent scaffolding, e.g. PLLA or PLGA, may be described, through comparison with a metallic material used to form a stent scaffolding, in some of the following ways. A suitable polymer has a low strength to weight ratio, which means more material is needed to provide an equivalent mechanical property to that of a metal. Therefore, struts must be made thicker and wider to have the strength needed. The scaffolding also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA.

Processing steps performed on, design changes made to a metal stent that have not typically raised concerns for, or require careful attention to unanticipated changes in the average mechanical properties of the material, therefore, may not also apply to a polymer stent due to the non-linear and sometimes unpredictable nature of the mechanical properties of the polymer under a similar loading condition. It is sometimes the case that one needs to undertake extensive validation before it even becomes possible to predict more generally whether a particular condition is due to one factor or another—e.g., was a defect the result of one or more steps of a fabrication process, or one or more steps in a process that takes place after stent fabrication, e.g., crimping. As a consequence, a change to a fabrication process, post-fabrication process or even relatively minor changes to a stent pattern design must, generally speaking, be investigated more thoroughly than if a metallic material were used instead of the polymer. It follows, therefore, that when choosing among different polymeric stent designs for improvement thereof, there are far less inferences, theories, or systematic methods of discovery available, as a tool for steering one clear of unproductive paths, and towards more productive paths for improvement, than when making changes in a metal stent.

It is recognized, therefore, that, whereas inferences previously accepted in the art for stent validation or feasibility when an isotropic and ductile metallic material was used, such inferences would be inappropriate for a polymeric stent. A change in a polymeric stent pattern may affect, not only the stiffness or lumen coverage of the stent in its deployed state supporting a lumen, but also the propensity for fractures to develop when the stent is crimped or being deployed. This means that, in comparison to a metallic stent, there is generally no assumption that can be made as to whether a changed stent pattern may not produce an adverse outcome, or require a significant change in a processing step (e.g., tube forming, laser cutting, crimping, etc.). Simply put, the highly favorable, inherent properties of a metal (generally invariant stress/strain properties with respect to the rate of deformation or the direction of loading, and the material's ductile nature), which simplify the stent fabrication process, allow for inferences to be more easily drawn between a changed stent pattern and/or a processing step and the ability for the stent to be reliably manufactured with the new pattern and without defects when implanted within a living being.

A change in the pattern of the struts and rings of a polymeric stent scaffolding that is plastically deformed, both when crimped to, and when later deployed by a balloon, unfortunately, is not as easy to predict as a metal stent. Indeed, it is recognized that unexpected problems may arise in polymer stent fabrication steps as a result of a changed pattern that would not have necessitated any changes if the pattern was instead formed from a metal tube. In contrast to changes in a metallic stent pattern, a change in polymer stent pattern may necessitate other modifications in fabrication steps or post-fabrication processing, such as crimping and sterilization.

One problem frequently encountered with a stent for delivery to a site in a body using a balloon is reliably retaining the stent on the balloon as it passes through tortuous anatomy. If the stent is not held on the balloon with sufficient force, it can slip off of the balloon during transit to the target site. For a metallic stent, there are several approaches proposed for increasing the retention of a stent to a balloon during transit to the target site. However, methods proposed thus far for retaining the polymer stent on a balloon are in need of improvement.

In light of the foregoing problems, there is a need for improving the retention of a polymer stent on a balloon while avoiding adverse effects on the mechanical characteristics of the load bearing, polymer scaffolding when the scaffolding is fully deployed to support a lumen.

SUMMARY OF THE INVENTION

It has been determined that more precise control of a crimping temperature aids in retention of a polymer stent on a balloon. A balloon expandable polymer stent made of a bioabsorbable material should benefit from processes disclosed herein. Polymers such as PLLA and PLGA have a semicrystalline structure. Control of temperature within a specific range for these materials, in relation to their glass transition temperature (Tg), can improve the retention force on a balloon without causing adverse effects on the polymer stent's strength and stiffness properties when it is later expanded by the balloon.

It is known that for a polymeric stent the glass transition temperature (Tg) of its matrix material has to be higher than physiological temperature (37° C.) in order to maintain enough radial strength after its implantation. PLLA material has a Tg at around 55-60° C. When a PLLA stent is crimped at room temperature, free polymer chain movement can hardly happen. It is therefore difficult to crimp a stent from a relatively large starting diameter to a designated final crimping diameter at, or below physiological conditions. One way proposed to solve the problem is to crimp a stent with a higher crimping force. This solution, however, will likely lead to more cracks when the stent is deployed, or when it is crimped. Crimping more slowly can reduce the number of cracks. However, deformation must be performed at a rate too slow for practical use in stent production.

The invention provides a medical device including a polymer stent crimped to a balloon. The invention also provides a process for crimping a polymer stent to a balloon. The polymer stent is expanded for placement within a lumen of the body by plastic deformation of the polymer scaffolding of the stent. The crimping process used to place the stent on the balloon includes heating the stent to a temperature that enables the polymer in the stent's scaffolding to deform to a reduced, crimping diameter without causing detrimental effects to the mechanical properties of the polymer material when it is later deployed within a lumen. The process increases the retention force, or resistance to dislodgment from the balloon when the medical device is delivered through tortuous anatomy.

In one embodiment, a heated crimper is used to reduce the diameter of the stent from the cut diameter to the final profile. Heat is used to raise the temperature of the stent allowing it to be deformed without damage and to retain the final shape. The temperature at which the process is run is, in the preferred embodiments, within a narrow range to achieve a desired outcome. For a stent made from PLLA material, it was found that the retention of the stent on the balloon was less than desired when it was crimped near room temperature. On the other hand, when the stent was crimped at higher temperatures (55° C. and above), it developed more cracks upon deployment, which affects the deployed strength of the stent.

In accordance with the foregoing objectives, there is provided a method for crimping a polymer stent to a balloon and an apparatus including a stent crimped to a catheter having a delivery balloon.

In one aspect of the invention there is a method for crimping a balloon-expanded stent scaffolding to a balloon, comprising the steps of: providing a tube comprising PLLA characterized by a glass transition temperature range having a lower limit of about 55° C.; radially or bi-axially expanding the tube to increase its radial strength; forming the scaffolding from the radially or bi-axially expanded tube, including the steps of forming; and crimping the scaffolding to the balloon while the scaffolding has a temperature of between, or between about 48° C. and 54° C. In other embodiments, the temperature range is, or about 48-50 degrees centigrade, or the temperature is, or about 48° C.

In another aspect of the invention, a method for crimping a balloon-expanded stent scaffolding to a balloon includes the steps of providing a tube comprising a polymer characterized by a glass transition temperature range having a lower limit of Tg-low; radially expanding the tube to increase its radial strength; forming the scaffolding from the radially-expanded tube; and crimping the scaffolding to the balloon while the scaffolding has a temperature of between about Tg-low and 15 degrees below Tg-low. The polymer may be PLLA or PLGA. The temperature range may be between about Tg-low and 10 degrees below Tg-low. The temperature range may be between about Tg-low and 5 degrees below Tg-low. The scaffold may have a circumferential series of closed cells having a W-shape and linear link struts connecting the W-shape cells. The balloon may be a PEBAX balloon. The crimping may reduce the scaffold size from a first diameter to a second diameter that is at least 2.5 times smaller than the tube diameter.

In another aspect of the invention, a medical device includes a polymer scaffolding crimped to a balloon; wherein the polymer scaffolding is retained to the balloon with a retention force of at least about 1.0 lbs.; wherein the polymer scaffolding is capable of being plastically expanded within a body lumen by the balloon and providing a therapeutic benefit to the body lumen including radially supporting the lumen, the plastically expanded polymer scaffolding having an outer diameter of at least about 2.5 times the outer diameter of the polymer scaffolding crimped to the balloon; and wherein after the polymer scaffolding has been plastically expanded the polymer scaffolding has a network of struts connecting ring elements, wherein the scaffolding includes circumferential series of closed cells having a W-shape and a linear link strut connecting the W-shape cells.

In another aspect of the invention, a medical device includes a polymer scaffolding crimped to a balloon; wherein the polymer scaffolding is retained to the balloon with a retention force of at least about 1.0 lbs.; wherein the polymer scaffolding is capable of being plastically expanded within a body lumen by the balloon and providing a therapeutic benefit to the body lumen including radially supporting the lumen, the plastically expanded polymer scaffolding having an outer diameter of at least about 2.5 times the outer diameter of the polymer scaffolding crimped to the balloon; wherein after the polymer scaffolding has been plastically expanded the polymer scaffolding has a network of struts connecting ring elements; and wherein the scaffolding includes ring structures forming a tubular body having a distal end, a proximal end, and an intermediate segment between the distal and proximal ends, the ring structures connected to each other by linear link struts that are oriented axially, the ring structures and link struts forming W-shape closed cells.

The scope of the methods and apparatus of the invention also encompass processes that crimp a scaffold as substantially described in US Pub. No. 2010/0004735 and US Pub. No. 2008/0275537. The thickness of the tube from which the scaffold is formed may have a thickness of between 0.10 mm and 0.18 mm, and more narrowly at or about 0.152 mm. The scaffold may be made from PLLA. And the scaffold may be crimped to a PEBAX balloon.

INCORPORATION BY REFERENCE

All publications and patent applications mentioned in this specification are herein incorporated by reference to the same extent as if each individual publication or patent application was specifically and individually indicated to be incorporated

DETAILED DESCRIPTION OF EMBODIMENTS

Figure 1:
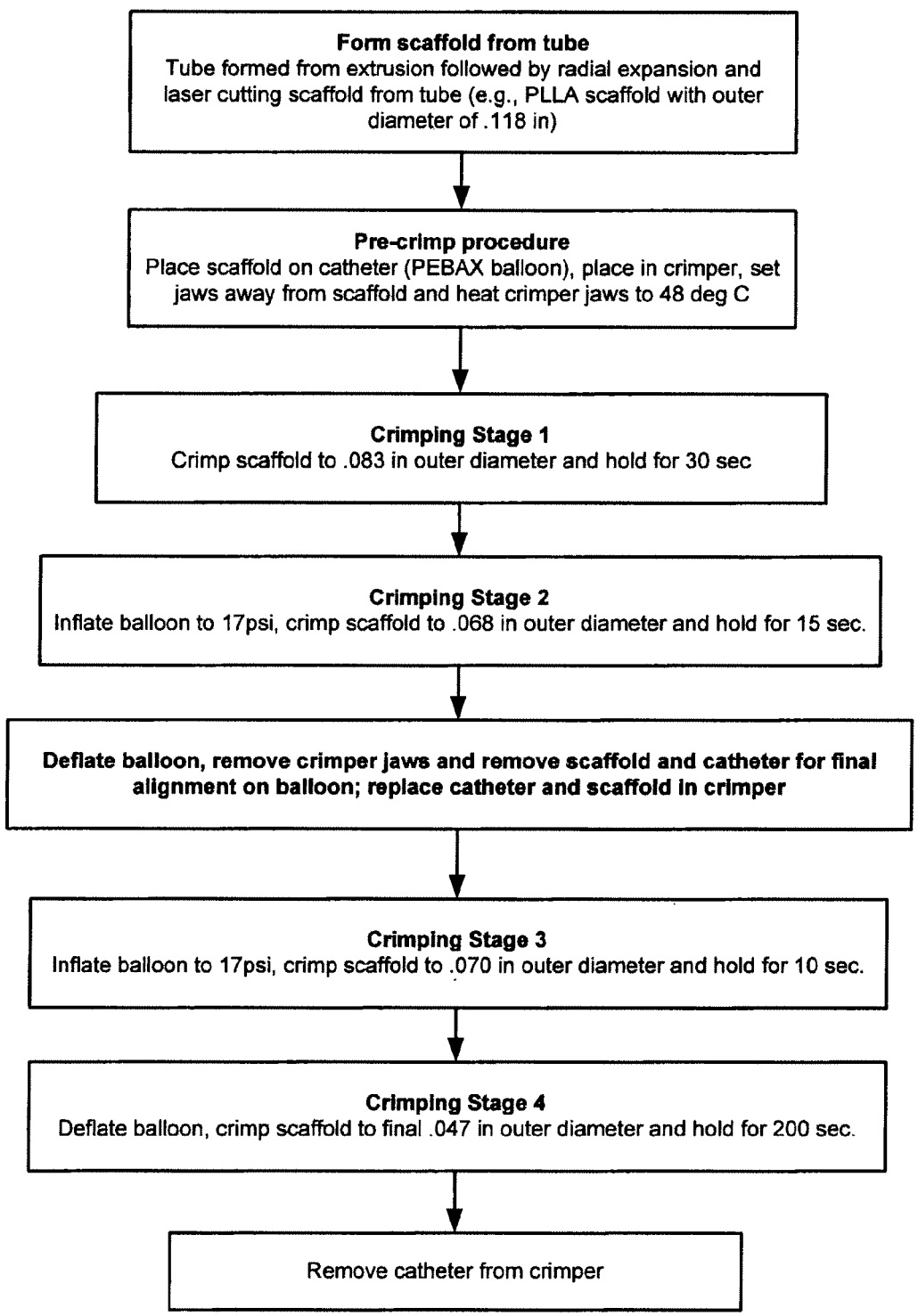
FIG. 1 shows a process for fabricating a scaffolding of a polymer stent and crimping the fabricated stent to a balloon according to the invention.

The "glass transition temperature," Tg, is the temperature at which the amorphous domains of a polymer generally change from a brittle, vitreous state to a solid deformable or ductile state at atmospheric pressure. In other words, the Tg corresponds to the temperature where the onset of noticeable segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

Poly(lactide-co-glycolide) (PLGA) and Poly (L-lactide) (PLLA) are examples of a class of semi-crystalline polymers that may be used to form the scaffolding for the stent structures described herein. PLLA is a homopolymer and PLGA is a co-polymer. The percentage of glycolide (GA) in a scaffold constructed of PLGA may vary, which can influence the lower range of Tg. For example, the percentage of GA in the matrix material may vary between 0-15%. For PLLA, the onset of glass transition occurs at about 55 degrees Celsius. With an increase of GA from about 0% to 15% the lower range for Tg for PLGA can be correspondingly lower by about 5 degrees Celsius.

In one embodiment, a tube is formed by an extrusion of PLLA. The tube forming process described in US Pub. No. 2010/00025894 may be used to form this tube. The finished, solidified polymeric tube of PLLA may then be deformed in radial and axial directions by a blow molding process wherein deformation occurs progressively at a predetermined longitudinal speed along the longitudinal axis of the tube. For example, blow molding can be performed as described in U.S. Publication No. 2009/0001633. This biaxial deformation, after the tube is formed, can produce noticeable improvement in the mechanical properties of the stent structural members cut from the tube without this expansion. The degree of radial expansion that the polymer tube undergoes characterizes the degree of induced circumferential molecular or crystal orientation. In a preferred embodiment, the radial expansion ratio or RE ratio is about 450% of the starting tube's inner diameter and the axial expansion ratio or AE ratio is about 150% of the starting tube's length. The ratios RA and AE are defined in US Pub. No. 2010/00025894.

The above scaffolding's outer diameter may be designated by where it is expected to be used, e.g., a specific location or area in the body. The outer diameter, however, is usually only an approximation of what will be needed during the procedure. For instance, there may be extensive calcification that breaks down once a therapeutic agent takes effect, which can cause the stent to dislodge in the vessel. Further, since a vessel wall cannot be assumed as circular in cross-section, and its actual size only an approximation, a physician can choose to over-extend the stent to ensure it stays in place. For this reason, it is preferred to use a tube with a diameter larger than the expected deployed diameter of the stent.

In one embodiment the ratio of deployed to fully crimped diameter is about 2.5. In this embodiment, the crimped diameter corresponds to an outer diameter that is only about 40% of the starting diameter. Hence, when deployed the drug eluting stent is expected to increase in size up to about 2.5 times its stowed or crimped diameter size.

In one particular example, a stent is formed from a biaxially expanded tube having an outer diameter of 3.5 mm, which approximately corresponds to a deployed diameter (the stent may be safely expanded up to 4.0 mm within a lumen). When crimped on the balloon, the stent has an outer diameter of 1.3 mm, or about 37% of the starting tube diameter of 3.5 mm.

As discussed earlier, fabrication of a balloon-expanded polymer stent presents challenges that are not present in metallic stents. One challenge, in particular, is the fabrication of a polymer scaffolding, which means the load bearing network of struts including connectors linking ring elements or members that provide the radial strength and stiffness needed to support a lumen. In particular, there exists ongoing challenges in fabricating a polymer scaffolding (hereinafter "scaffolding") that is capable of undergoing a significant degree of plastic deformation without loss of strength, e.g., cracks or fracture of struts. In the disclosed embodiments, a polymer scaffolding is capable of being deformed from a crimped diameter to at least 2.5 times the crimped diameter without significant loss of strength. Moreover, the polymer scaffolding is retained on a delivery balloon with a retention force that is significantly higher than previous methods of stent retention for a polymer stent.

The invention addresses the unique challenges presented by a polymer stent that needs to be retained on a balloon. These challenges are present for several reasons. First, there is less space available between struts in a crimped state, which prevents balloon material from extending between struts. As a result, there is less abutment or interference between struts and balloon material, which interference/abutment has previously been relied upon to increase the retention force of the stent on a balloon. This condition is a result of the need to fabricate wider and thicker struts for the polymer stent, as compared to a metal stent, so as to provide adequate, deployed radial strength. Second, a polymer, unlike a metal, is far more sensitive to changes in temperature. The art has previously relied on heat to retain a metal stent on a balloon. However, the temperatures that have previously been found effective for stent retention fall within a Tg of the polymer. Such temperature ranges have, therefore, been avoided since heating of a polymer scaffolding to within, or above Tg induces significant changes in the molecular orientation of the polymer material that result in loss of strength when the scaffolding is plastically deformed to its deployed diameter.

The art has previously devised methods for retaining a polymer stent on a delivery balloon in response to these challenges. In one example, the stent is crimped to the delivery balloon at a temperature well below the polymer's Tg. Then the stent, disposed between ends of the balloon, is thermally insulated from the balloon's ends. The ends of the balloon are then heated to about 185 degrees Fahrenheit to expand the diameter of the balloon material at its ends. The expanded balloon ends form raised edges abutting the stent ends to resist dislodgment of the stent from the balloon. In one example, this process provided a retention force of about 0.35 lb. for a Poly (L-lactide) (PLLA) scaffolding crimped to a polymide-polyether block co-polymer (PEBAX) balloon.

As explained more fully below, it was found, unexpectedly, that there is a certain degree of beneficial movement between interconnected polymer chains of a stent structure heated to temperatures just below Tg of the polymer when the stent is being crimped to a balloon, versus the same stent crimped to the balloon at a lower temperature, such as room temperature. For example, for a controlled temperature of between about 48 and 54 degrees, 48-50 degrees or 48 degrees Celsius it was found that a PLLA stent crimped to a balloon exhibited noticeable improvement in the retention force of the stent on the balloon, while not concomitantly producing unacceptable side effects for the deployed stent, e.g., excessive cracking or void formation, fracture or loss of memory in the material affecting its deployed radial stiffness qualities.

One problem encountered with fabrication of a stent for delivery to a site in a body using a balloon is the ability of the stent to be safely crimped to the balloon so that an adequate retention force is established between the stent and balloon. A "retention force" for a stent crimped to a balloon means the maximum force, applied to the stent along the direction of travel through a vessel, that the stent-balloon is able to resist before dislodging the stent from the balloon. The retention force for a stent on a balloon is set by a crimping process, whereby the stent is plastically deformed onto the balloon surface to form a fit that resist dislodgment of the stent from the stent. Factors affecting the retention of a stent on a balloon are many. They include the extent of surface-to-surface contact between the balloon and stent, the coefficient of friction of the balloon and stent surfaces, and the degree of protrusion or extension of balloon material between struts of the stent. For a metal stent there are a wide variety of methods known for improving the retention force of a stent on a balloon via modification of one or more of the foregoing properties; however, many are not suitable or of limited usefulness for a polymeric stent, due to differences in mechanical characteristics of a polymer stent verses a metal stent as discussed earlier. Most notable among these differences is brittleness of the polymer material suitable for balloon-expanded stent fabrication, verses that of a metal stent. Whereas a metal stent may be deformed sufficiently to obtain a desired retention force, the range of deformation available to a polymer stent, while avoiding cracking or fracture-related problems, by comparison, is quite limited.

For polymeric stents, the glass transition temperature (Tg) of its matrix material has to be higher than physiological temperatures (37 degrees Celsius) in order to maintain radial strength after implantation. A stent formed from PLLA has a Tg of about 55-60 degrees Celsius. When a PLLA stent is crimped to a balloon at around 25 degrees Celsius, a free polymer chain movement hardly occurs. As a consequence, the PLLA is brittle and susceptible to crack formation. Moreover, at this temperature, well below Tg, the stent will tend to recoil or revert towards its starting diameter of the tube, to a certain degree, due to the memory in the material. In addition, when the stent is deformed during crimping, the induced strain in the polymer matrix will cause the stent to enlarge to a certain degree once the crimping force is removed, since there will be some percentage of elastic deformation when the stent is crimped to the balloon, which causes the stent to revert towards its original diameter when the crimping force is relieved. This degree of elastic recoil, so to speak, limits the amount of retention of the stent on the balloon since the degree of contact between stent and balloon is reduced. Stated somewhat differently, when there is elastic recoil to a larger diameter, the normal force the stent imparts on the balloon while the crimping force is applied, which is proportional to magnitude of the retention force, decreases once the crimper is removed due to the percentage of elastic recoil in the stent.

One solution is to increase the retention force beyond that of the final crimped diameter. However, when crimping to a diameter of about 2.5 times less than a starting diameter to increase the retention force, consideration must given to increased instances of crack formation in the stent. These cracks can render the stent incapable of functioning properly when fully deployed by the balloon. There can be significant loss in radial stiffness and strength resulting in fracture. As a consequence, crack or loss of strength avoidance is an ongoing concern when efforts are made to a crimp polymer stent sufficiently from a staring diameter, preferably near the deployed diameter, to a designated final, crimping diameter to increase the retention force.

A polymer material's resistance to fracture, particularly when deformed at temperatures well below Tg, is dependent upon the rate at which the material is deformed. However, the inventors found that a solution to the stent retention/cracking problem described above is not found by simply decreasing the rate at which the stent is crimped onto the balloon. The rates that would produce noticeable improvements in stent retention without loss of strength would be infeasible for stent production.

In finding a solution to the stent retention problem, it was initially unclear whether stent retention, without detrimental damage being done to the stent, might be improved by increasing or varying balloon pressure during crimping, initiating stages of stent crimping including different rates, interim and final hold times at various crimper diameters, e.g., pre-crimping steps, or increasing the temperature of the stent while it was being crimped, or a combination of these factors. A preliminary study was conducted to determine whether modification of one or more of these factors in a polymer scaffold crimping process might improve stent retention. Thus, factors including temperature, hold time, balloon pressure force, pressure sequence, pressure initiation size, and speed of crimping were initially studied and results collected and studying under a multi-factored statistical approach to identify the key factors altering scaffold retention to a balloon. For this preliminary study, an iris crimper was used to crimp the stent. The scaffold was heated by heating the crimper jaws, although the scaffold may alternatively be heated by a forced hot air gas or heated fluid for expanding the balloon.

Based on this multi-factored study it was hypothesized that a carefully chosen temperature range might improve results, which came as a surprise. It was previously believed there would be little, or no benefit to heating a scaffold during crimping because either a raised temperature would induce molecular motion destroying the chain alignment needed to give the scaffold its deployed strength properties, or the temperature was too low to affect either the scaffold or the balloon.

A more narrow-focused study was conducted to identify a temperature range that might produce a significant difference in scaffold retention force without causing adverse effects on the deployed or crimped scaffold. TABLES 1 and 2, below, provide statistics for a retention force of a polymer scaffold-balloon as a function of the scaffold temperature during crimping. The crimping process was similar to that described in FIG. 1. Two studies were conducted, one for scaffold temperatures of 37-48° C. and the other for scaffold temperatures of 48-80° C., respectively. Both tests evaluated the retention force for a PLLA scaffolding having the pattern described in US 2010/0004735 and crimped to a PEBAX balloon. More specifically, a first study included conducting several trials at each of 37° C., 42.5° C. and 48° C. and a second study included conducting several trials at each of 48° C., 55° C., 65° C. and 80° C.

TABLES 1 and 2 show the mean and standard deviation in retention force (obtained using a standard pull-off test procedure) for a PLLA scaffolding having the pattern described in US 2010/0004735 and crimped to a PEBAX balloon. "Number" refers to the number of trials run at the corresponding scaffold temperatures.

TABLE 1

| Temp (Celsius) | Number | Mean | Std Dev |
|---|---|---|---|
| 48 | 11 | 1.18 | 0.33 |
| 55 | 9 | 1.16 | 0.15 |
| 65 | 8 | 1.41 | 0.17 |
| 80 | 4 | 2.03 | 0.20 |

TABLE 2

| Temp (Celsius) | Number | Mean | Std Dev |
|---|---|---|---|
| 37 | 20 | 0.74 | 0.19 |
| 42.5 | 21 | 1.24 | 0.11 |
| 48 | 13 | 1.24 | 0.14 |

Modifying the pressure and hold time of the scaffolding on the stent for crimping temperatures of 40° and 55° C. improved the scaffold retention. However, modifying these parameters outside of this range produce little change. Specifically, for a 40° and 55° C. range of crimping the retention may be improved by balloon pressure being increased to raise the balloon diameter to the pre-crimp stent diameter, then the stent was crimped on the balloon to a final crimp diameter while pressure is released. Additionally, the stent may be crimped down to an intermediate diameter, then the balloon is deflated then re-inflated, followed by crimping the stent down to a final crimp diameter.

Figure 2:
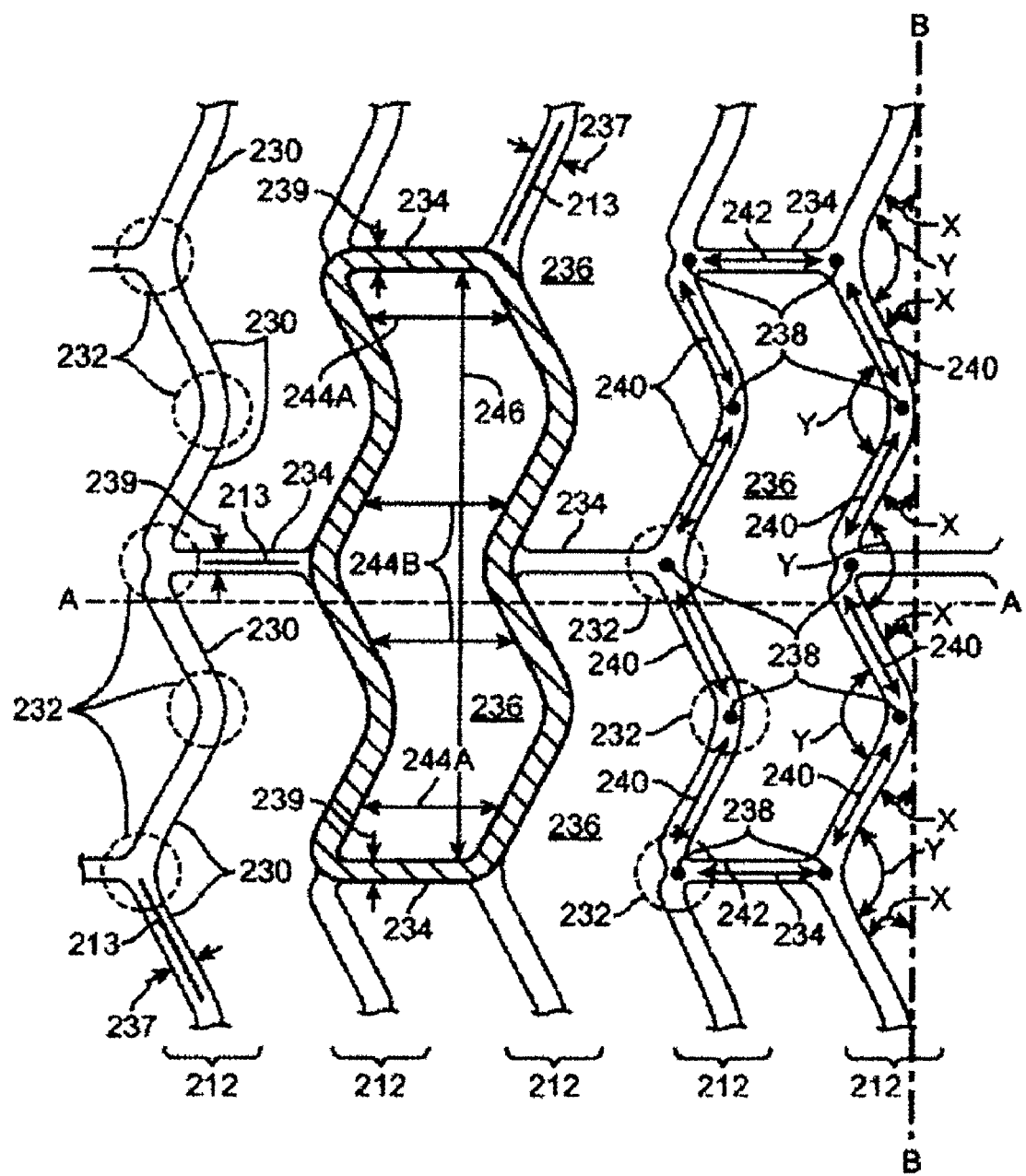
FIG. 2 is planar view of a portion of a polymer stent scaffolding that was crimped to a balloon according to aspects of the invention. This view describes the stent pattern of the load-bearing structure of the scaffolding of the fully deployed stent that is crimped to a balloon according to the process of FIG. 1.

FIG. 1 is a process diagram illustrating the steps used to fabricate a polymer scaffold and crimp the scaffold to a balloon. In this example, a scaffold was formed from a radially expanded tube of PLLA. The scaffold had a strut pattern as shown in FIG. 2. The struts had a thickness of about 0.152 mm and the balloon used was a PEBAX balloon. An iris crimper was used to crimp the scaffold to the balloon.

A crimping process may proceed as follows. In preparation for the crimping operation, the crimp head diameter is moved to an intermediate position that is larger than the scaffold starting outer diameter (OD). The temperature of the jaws is raised to, or to about 48° C. and is allowed to stabilize at that temperature. A delivery catheter (holding the balloon) is chosen with the correct size to fit the scaffold.

The scaffold is placed onto the balloon catheter with the distal portion of the scaffold aligned with the distal portion of the catheter. The catheter is then placed onto a sliding alignment carriage. A final adjustment is made to the scaffold to position it between balloon markers on the catheter. The scaffold and catheter is moved into the crimp jaws, by sliding the carrier forward.

The cycle is initiated by the operator. As an example, for a 3.0×18 mm scaffold, the ID of the crimp head moves to a diameter of 0.083" where it remains for 30 seconds. This is stage 1. The system moves automatically to stage 2 where the head moves to an ID of 0.068" and is held for 15 seconds. During this stage, the balloon catheter is inflated to 17 psi. After this stage is complete, the balloon is deflated and the crimp head is opened to allow the catheter to be removed. The scaffold receives a final alignment to the balloon markers. The scaffold and balloon are placed back into the crimp head. The operator initiates stage 3 where the head is reduced to 0.070" diameter for 10 seconds. During this stage 3, the balloon is also inflated to 17 psi. Once complete, the machine moves automatically to the stage 4, where the balloon is deflated and the crimp head ID is reduced to 0.047" and is held for 200 seconds. When this fourth and final stage is complete, the head opens and the catheter and scaffold removed. The scaffold is retained on the balloon and is immediately placed into a sheath, to prevent recoil of the scaffold.

The above study was conducted for PLLA. Similar results are contemplated for PLGA, if Tg for the different material is taken into consideration and assuming other characteristics of the process and scaffold pattern. For PLGA having % GA of about 5% the temperature ranges for crimping may be between about 46 to 53 degrees Celsius. For PLGA having % GA of about 15% the temperature ranges for crimping are about 43 to 50 degrees Celsius.

Based on the foregoing results, the following conclusions were reached. When the scaffold is crimped to a balloon while being heated to temperatures well within the range of Tg for the scaffold polymer, there is a greater tendency for polymer chain re-alignment to occur that will result in loss of strength when the scaffold is later deployed. Unacceptable crack formation (either in the number or extent of cracks), voids or outright fracture was observed in subsequent testing. It should be noted that acceptable scaffolds have cracks. The degree of crack formation that cause a scaffold to be rejected is based on tests conducted on the scaffold when fully deployed, e.g., accelerated aging, fatigue, cyclic loading and static load tests and including a visual inspection of the scaffold.

It should be noted, therefore, that some degree of crack, or void formation is permissible and indeed expected. Validation of a crimping process, therefore, generally cannot be made by simply inspecting or counting the number of cracks or voids. Testing is needed to establish, to a reasonable degree of confidence, a relationship between the locations and nature of the imperfections at those locations in the scaffold and its ability to function properly. Mechanical testing is needed to assess the degree of structural integrity in the deployed polymer scaffolding. Then, relying on statistics a determination may be made as to the type, number and/or location of cracks/voids that distinguish between an acceptable and unacceptable scaffold. A scaffold, despite the presence of one or more cracks and/or voids, may then be deemed capable of being plastically expanded within a body lumen by the balloon to which it is crimped. As such, the scaffold is deemed capable of providing a therapeutic benefit to the body lumen including radially supporting the lumen despite the presence of one or more cracks/voids.

If the crimping temperature is raised too high relative to the Tg of the polymer, the memory of the matrix material at the starting tubing diameter is being removed, or reformed as the scaffold is deformed. As a consequence, when the scaffold is later expanded under physiological conditions, e.g., body temperature, it becomes more susceptible to crack formation due to its brittle properties at body temperatures and lack of chain alignment from its starting diameter. Retention force and scaffold integrity when crimped to the balloon generally improves at higher temperatures, however, the scaffold loses its structural integrity when later deployed if the temperature is raised too high relative to Tg. On the other hand, when the scaffold is heated to temperatures below about 15 degrees Celsius of the glass transition temperature, or not heated at all, there is no noticeable improvement in scaffold retention. And if the crimping force is increased to improve scaffold retention at these temperatures, loss in strength occurs as cracks appear in the crimped and deployed scaffold. It was concluded, therefore, that for a temperature below about 15 degrees from Tg the scaffold exhibited more or less the same degree of fracture toughness it would exhibit under physiological conditions.

Surprisingly, when the temperature range was raised to within a range of about 15 degrees below and up to about Tg there was a noticeable and consistent improvement in scaffold retention force, without unacceptable loss in structural integrity for the deployed scaffold. It is believed that when the polymer scaffold was crimped at a temperature slightly below its Tg (e.g., from 5 to 15 degrees Celsius below Tg), there are very short chains of the matrix material that are able to freely move to assist in the deformation of the scaffold without exceeding material stress limits. At the same time, the longer chains of the matrix substantially maintain their alignment, and, thus, stay intact without losing their orientation set when the starting tube was expanded. By doing so, the scaffold may be crimped down to a diameter for good scaffold retention, while the orientation of a majority of polymer chains would be the same to ensure desirable strength and fracture toughness in the final product, i.e., when the stent is deployed to support a vessel.

The improved scaffold retention may also be explained in terms of the balloon-scaffold interaction. As noted above, when the temperature was raised to within the range of Tg, there was improved scaffold retention ability. When the temperature was below about 15 degrees Celsius of Tg there was no improvement (same crimping force used in both cases). In the former case, it is believed that with the increased temperature there is greater cohesion or contact between the scaffold and balloon resulting from the increased temperature. As the scaffold and balloon material temperatures increase, the material becomes more compliant resulting in stronger adherence between the two surfaces, or greater surface-to-surface contact. As a result, the retention force increases. For the tests, a PEBAX balloon was used.

While trends seen in the test data were in some ways hypothesized, it was far from clear whether there existed a degree of polymer chain movement induced within a temperature range that would make much, if any difference in the outcome without also producing undesirable side effects. The stress-strain states of a polymer scaffold expanded to 2.5 times its starting diameter (i.e., crimped to deployed) are difficult to understand through the empirical data, much less through analytic models. Moreover, the understanding in the art, as known to inventors, was that when a PLLA and PLGA scaffold is deformed, the effects of temperature on scaffold properties, or stent scaffold retention would be minimal unless the temperature range fell within Tg. Notwithstanding this common understanding, the inventors found that when the temperature was raised to, or near Tg, there was consistent improvement in the scaffold retention force for the polymer scaffold when crimped to the balloon, and without loss in structural integrity for the deployed scaffolding.

As noted above, in a preferred embodiment a stent scaffold has the stent pattern described in U.S. application Ser. No. 12/447,758 (US 2010/0004735) to Yang & Jow, et al. Other examples of stent patterns suitable for PLLA are found in US 2008/0275537. FIG. 2 shows a detailed view of an intermediate portion 216 of a strut pattern 200 depicted in US 2010/0004735. The intermediate portion includes rings 212 with linear ring struts 230 and curved hinge elements 232. The ring struts 230 are connected to each other by hinge elements 232. The hinge elements 232 are adapted to flex, which allows the rings 212 to move from a non-deformed configuration to a deformed configuration. Line B-B lies on a reference plane perpendicular to the central axis 224 depicted in US 2010/0004735. When the rings 212 are in the non-deformed configuration, each ring strut 230 is oriented at a non-zero angle X relative to the reference plane. The non-zero angle X is between 20 degrees and 30 degrees, and more narrowly at or about 25 degrees. Also, the ring struts 230 are oriented at an interior angle Y relative to each other prior to crimping. The interior angle Y is between 120 degrees and 130 degrees, and more narrowly at or about 125 degrees. In combination with other factors such as radial expansion, having the interior angle be at least 120 degrees results in high hoop strength when the stent is deployed. Having the interior angle be less than 180 degrees allows the stent to be crimped while minimizing damage to the stent struts during crimping, and may also allow for expansion of the stent to a deployed diameter that is greater than its initial diameter prior to crimping. Link struts 234 connect the rings 212. The link struts 234 are oriented parallel or substantially parallel to a bore axis of the stent. The ring struts 230, hinge elements 232, and link struts 234 define a plurality of W-shape closed cells 236. The boundary or perimeter of one W-shape closed cell 236 is darkened in FIG. 2 for clarity. In FIG. 2, the W-shapes appear rotated 90 degrees counterclockwise. Each of the W-shape closed cells 236 is immediately surrounded by six other W-shape closed cells 236, meaning that the perimeter of each W-shape closed cell 236 merges with a portion of the perimeter of six other W-shape closed cells 236. Each W-shape closed cell 236 abuts or touches six other W-shape closed cells 236.

Referring to FIG. 2, the perimeter of each W-shape closed cell 236 includes eight of the ring struts 230, two of the link struts 234, and ten of the hinge elements 232. Four of the eight ring struts form a proximal side of the cell perimeter and the other four ring struts form a distal side of the cell perimeter. The opposing ring struts on the proximal and distal sides are parallel or substantially parallel to each other. Within each of the hinge elements 232 there is an intersection point 238 toward which the ring struts 230 and link struts 234 converge. There is an intersection point 238 adjacent each end of the ring struts 230 and link struts 234. Distances 240 between the intersection points adjacent the ends of rings struts 230 are the same or substantially the same for each ring strut 230 in the intermediate portion 216 of the strut pattern 200. The distances 242 are the same or substantially the same for each link strut 234 in the intermediate portion 216. The ring struts 230 have widths 237 that are uniform in dimension along the individual lengthwise axis 213 of the ring strut. The ring strut widths 234 are between 0.15 mm and 0.18 mm, and more narrowly at or about 0.165 mm. The link struts 234 have widths 239 that are also uniform in dimension along the individual lengthwise axis 213 of the link strut. The link strut widths 239 are between 0.11 mm and 0.14 mm, and more narrowly at or about 0.127 mm. The ring struts 230 and link struts 234 have the same or substantially the same thickness in the radial direction, which is between 0.10 mm and 0.18 mm, and more narrowly at or about 0.152 mm.

As shown in FIG. 2, the interior space of each W-shape closed cell 236 has an axial dimension 244 parallel to line A-A and a circumferential dimension 246 parallel to line B-B. The axial dimension 244 is constant or substantially constant with respect to circumferential position within each W-shape closed cell 236 of the intermediate portion 216. That is, axial dimensions 244A adjacent the top and bottom ends of the cells 236 are the same or substantially the same as axial dimensions 244B further away from the ends. The axial and circumferential dimensions 244, 246 are the same among the W-shape closed cells 236 in the intermediate portion 216.

It will be appreciated from FIG. 2 that the strut pattern for a stent that comprises linear ring struts 230 and linear link struts 234 formed from a radially expanded and axially extended polymer tube. The ring struts 230 define a plurality of rings 212 capable of moving from a non-deformed configuration to a deformed configuration. Each ring has a center point, and at least two of the center points define the stent central axis. The link struts 234 are oriented parallel or substantially parallel to the stent central axis. The link struts 234 connect the rings 212 together. The link struts 232 and the ring struts 230 defining W-shape closed cells 236. Each W-shaped cell 236 abuts other W-shaped cells. The ring struts 230 and hinge elements 232 on each ring 212 define a series of crests and troughs that alternate with each other. Each crest on each ring 212 is connected by one of the link struts 234 to another crest on an immediately adjacent ring, thereby forming an offset "brick" arrangement of the W-shaped cells.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for crimping a balloon-expanded stent scaffolding to a balloon, comprising the steps of:
    providing a tube comprising PLLA-(Poly(L-lactide)) characterized by a glass transition temperature range having a lower limit of about 55° C.;
    radially expanding the tube to increase its radial stiffness;
    forming the scaffolding from the radially-expanded tube, including the steps of forming a circumferential series of closed cells having a W-shape and linear link struts connecting the W-shape cells; and
    crimping the scaffolding to the balloon while the scaffolding has a temperature of between about 48° C. and 54° C.;
    wherein in a first crimping step the scaffolding is crimped to a first diameter by placing a crimper head at a first diameter and holding the crimper head at the first diameter while the balloon is inflated to a first pressure.

2. The method of claim 1, wherein the temperature range is about 48-50 degrees centigrade.

3. The method of claim 2, wherein the formed scaffolding has a diameter about 2.5 times greater than its diameter after performing the crimping step.

4. The method of claim 3, wherein the temperature is about 48° C.

5. The method of claim 1, wherein in a second crimping step the crimper head is moved to a second diameter, less than the first diameter, and holding the crimper head at the second diameter while the balloon is inflated to a second pressure.

6. The method of claim 5, wherein after the second crimping step performing a third crimping step including the crimper head being moved to a third diameter, less than the second diameter, and holding the crimper head at the third diameter.

7. The method of claim 1, wherein a final crimped diameter for the scaffolding has a retention force that is greater than 1.0 lbs and the final crimped diameter is at least 2.5 times less than the scaffold diameter before crimping.

8. A method for crimping a scaffolding to a balloon, comprising the steps of:
    providing the scaffolding from a radially-expanded tube comprising a polymer characterized by a glass transition temperature (Tg), the scaffolding having a pre-crimp scaffolding diameter; and
    crimping the scaffolding to the balloon while the scaffolding has a temperature of between about Tg-low and 15 degrees below Tg-low, including the steps of:
        raising the balloon pressure to increase the balloon diameter to about the pre-crimp scaffolding diameter, and
        crimping the scaffolding to a final crimp diameter while balloon pressure is being released.

9. The method of claim 8, wherein the scaffolding diameter is crimped to an intermediate diameter, the balloon is deflated then re-inflated while the scaffolding has the intermediate diameter, followed by crimping the scaffolding down to a final crimp diameter.

10. The method of claim 8, wherein the final crimped diameter is at least 2.5 times less than the pre-crimp diameter.

11. The method of claim 10, wherein the scaffolding has a circumferential series of closed cells having a W-shape and linear link struts connecting the W-shape cells.

* * * * *